US006823043B2

(12) United States Patent
Fewster et al.

(10) Patent No.: US 6,823,043 B2
(45) Date of Patent: Nov. 23, 2004

(54) DETERMINATION OF MATERIAL PARAMETERS

(75) Inventors: Paul F. Fewster, Brighton (GB); Gareth A. Tye, Crawley (GB)

(73) Assignee: Panalytical B.V., Almelo (NL)

( * ) Notice: Subject to any disclaimer, the term of this patent is extended or adjusted under 35 U.S.C. 154(b) by 0 days.

(21) Appl. No.: 10/179,323

(22) Filed: Jun. 25, 2002

(65) Prior Publication Data

US 2003/0012337 A1 Jan. 16, 2003

(30) Foreign Application Priority Data

Jul. 10, 2001 (GB) .............................................. 0116825

(51) Int. Cl.[7] .......................................... G01N 23/201
(52) U.S. Cl. ............................. 378/86; 378/88; 378/89
(58) Field of Search ............................. 378/86, 88, 89, 378/70, 50, 54, 45, 53, 83

(56) References Cited

U.S. PATENT DOCUMENTS

| | | | |
|---|---|---|---|
| 5,442,676 A | 8/1995 | Fewster | 378/72 |
| 5,530,732 A | 6/1996 | Takemi | 378/73 |
| 5,740,226 A | 4/1998 | Komiya et al. | 378/70 |
| 6,453,006 B1 * | 9/2002 | Koppel et al. | 378/86 |

OTHER PUBLICATIONS

A.D. Daine, A.1,3 Veldhuis 1 D.K.G. de Boer 2 A.J.G. Leenaers 2 and L.M.C. Buydens 1 Katholieke Universiteit Nijmegen, Toernooiveld 1, 6525 ED Nijmegen, email: adane@sci.kun.nl, Philips Research Laboratories, Professor Holstlaan 4, 5656 AA Eindhoven, Jan. 30, 1998.

Dane, A.D., et al., "Application of genetic algorithms for characterization of thin layered materials by glancing incidence x-ray reflectometry" Physica B. vol. 253, 1998 pp. 254–268.

Jos G.E. Klappe et al., "Fitting of Rocking Curbes From Ion–Implanted Semiconductors", Journal of Applied Crystallography ISSN 0021–8898 (1994). 27, (pp. 103–110).

Vaclav Holy et al., "High–Resolution X–Ray Scattering from Thin Films and Multilayers", Springer Tracts in Modern Physics (pp. 88–103).

Paul F. Fewster, "X–Ray Scattering From Semiconductors", Copyright 2000 by Imperial College Press (pp. 196–211).

* cited by examiner

Primary Examiner—Craig E. Church
Assistant Examiner—Chih-Cheng Glen Kao
(74) Attorney, Agent, or Firm—Blakely Sokoloff Taylor & Zafman

(57) ABSTRACT

A method for determining parameters of a material includes comparing a range of an actual x-ray scattering profile with a range of an expected x-ray scattering profile for a material sample. The expected profile is modified to match the actual profile and this is then repeated with an ever-larger range of the profiles until two profiles match across the whole of their profile. From the last modified expected profile the parameters of the material are determined.

9 Claims, 3 Drawing Sheets

DETERMINATION OF MATERIAL PARAMETERS

BACKGROUND

1. Field

This invention relates to a method for determining parameters of a material. In particular this invention relates to the use of x-ray scattering to determine the parameters of a material. The material may, for example, be a semiconductor sample that consists of a number of very thin layers. The parameters of particular interest are the composition and thickness of these layers.

2. Description of the Related Art

It is well known to analyse a material sample by submitting it to x-ray analysis to produce an x-ray scattering profile. When analysing a semiconductor substrate the actual profile is compared to an expected profile for an approximation of the material. If the two profiles are different, then the expected profile is modified on the basis of error data generated from comparing the two profiles. This process is then repeated until the two profiles substantially match, at which point the parameters of the material under analysis are known from the parameters used for the last modified expected profile.

This technique is satisfactory for a large number of applications, but has certain weaknesses. Fitting predicted models to experimental data can be complex especially when physical mechanism giving rise to the profile is very sensitive to the wanted parameters. X-ray scattering procedures fall into this category and require model modification and comparisons in an iterative procedure to achieve the parameters of interest. The existence of several minima in the discrepancies between the calculated and experimental profiles often leads to incorrect solutions in an automatic refinement process. A number of methods of improving this process have been proposed.

U.S. Pat. No. 5,442,676 relates to a method of determining a given characteristic of a material sample. Measurements are made on a sample to obtain an experimental profile having structural features determined at least in part by the given characteristic and an expected profile is calculated for the sample using selected parameters. A degree of smoothing is applied to the experimental profile to reduce the structural features thereby producing a smoothed experimental profile and the same degree of smoothing is applied to the calculated profile to produce a smoothed calculated profile. The smoothed calculated profile is compared with the smoothed experimental profile to determine the difference between the smoothed profiles. The calculated profile is then modified by varying at least one of the parameters until the smoothed modified profile fits the smoothed experimental profile. The above steps are then repeated with the modified calculated profile using each time a degree of smoothing less than the previous time so that the structural features return and the final modified calculated profile provides a desired fit to the experimental profile thereby enabling the given characteristic to be determined from the parameters used for the final modified profile. This should generally reduce the computation time required for the fitting procedure, especially if the initial guess is not close. In addition, the smoothing of the experimental and calculated profiles removes or at least reduces the possibility of satellite or false minima occurring in the fitting procedure which would otherwise increase the possibility of a false result or at least cause an unnecessary increase in computation time.

In the paper "Application of genetic algorithms for characterization of thin layered materials by glancing incidence x-ray reflectometry" by A. D. Dane et al., published 30 Jan. 1998 in the journal Physica B, the authors propose the use of known genetic algorithms for the characterisation of materials. The genetic algorithm is an optimisation technique and is used during the process of comparing the two x-ray profiles and modifying of the calculated profile. The genetic algorithm is able to find good fits within a single run. This reduces the amount of human effort and expertise required for analysing reflectivity measurements. Furthermore, it reduces the probability of overlooking feasible solutions.

U.S. Pat. No. 5,530,732 discloses a method of determining the composition and thicknesses of metamorphic layers at heterointerfaces of periodic laminated structures, such as multiple quantum well structures. An x-ray diffraction pattern of the actual structure is measured and a theoretical x-ray diffraction pattern is calculated using dynamic x-ray theory and giving special attention to x-ray diffraction fringes near a satellite peak in the pattern. The respective positions of the main peak and the satellite peak on the theoretical pattern are fitted to the measured pattern first. The thicknesses and compositions of the metamorphic layers are adjusted in a recursive analysis until the calculated pattern agrees with the measured pattern, thereby providing an accurate analysis of laminated periodic structures.

However, when the data is over a large angular range and full of fringing then the density of local minima becomes very large. A typical local minimum condition is shown in FIG. 3. The process of trying to fit automatically the whole profile to the expected profile (FIG. 2) is rendered virtually impossible by the fact that some of the fringes overlap (when the profiles are overlaid) and give false minimum.

SUMMARY

It is therefore an object of the invention to provide an improved method for determining parameters of a material.

According to the present invention, there is provided a method for determining parameters of a material, comprising a) calculating an expected x-ray scattering profile for an approximation of said material, b) obtaining an actual x-ray scattering profile of said material, c) comparing a selected range of said expected x-ray scattering profile with a selected range of said actual x-ray scattering profile and generating error data based upon the differences between the profiles over the selected ranges, d) modifying said expected x-ray scattering profile according to said error data, e) repeating steps c) and d) until said range of the expected x-ray scattering profile substantially matches said range of the actual x-ray scattering profile, f) expanding said range, g) repeating steps c) to f) until said expected x-ray scattering profile substantially matches said actual x-ray scattering profile, and thereby determining parameters of the material from the parameters used for the last modified expected x-ray scattering profile.

Owing to the invention, it is possible to provide a method for determining parameters of a material that, by first fitting a range of the expected x-ray scattering profile to the actual x-ray scattering profile, reaches an accurate fit in a relatively short period of time, for even the more complicated x-ray scattering profiles.

Advantageously, prior to the method step c), a degree of smoothing is applied to the profiles. By applying smoothing to the profiles, it is easier and faster to match the two profiles. Preferably, the modifying of method step d) is achieved by the use of an iterative algorithm. It is also desirable, prior to the method step c) to first use a genetic algorithm to modify the expected x-ray scattering profile.

When selecting the range in the first run of the matching, it is advantageous that the range is the less sensitive region of the profile. The technique works especially well when the x-ray scattering profiles are x-ray reflectometry profiles and when the range includes the portion of the x-ray scattering profile where the scattered intensity is falling rapidly from the critical edge.

BRIEF DESCRIPTION OF THE DRAWINGS

Embodiments of the invention will now be described, by way of example only, with reference to the accompanying drawings, in which.

DETAILED DESCRIPTION

Figure 1:
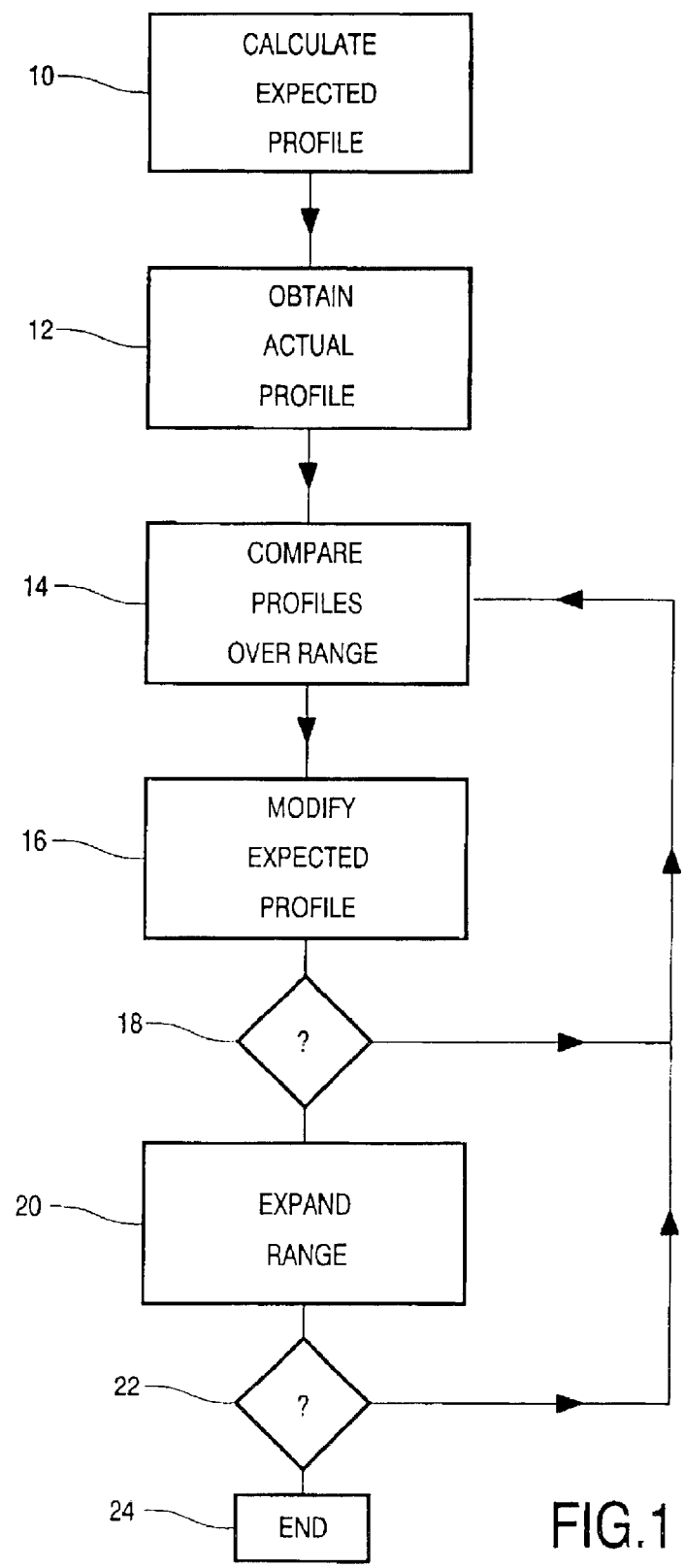
FIG. 1 is a flowchart of a method for determining parameters of a material.

In order to determine parameters of a material, which may be, for example, a semiconductor sample, an analysis using x-ray scattering techniques can be performed. Such techniques are well known from, for example, "High Resolution X-Ray Scattering from Thin Films and Multilayers" by V. Holy et al., published 1999 by Springer-Verlag. FIG. 1 is a flowchart of a method of determining parameters of such a material.

The first step 10 is to calculate an expected x-ray scattering profile for an approximation of the material. If the analysis is being carried out as, for example, a quality control exercise on a semiconductor fabrication unit, then the user carrying out the analysis will have a good idea of the components of the sample. If the user does not know the components of the sample, then a best guess must be made from the information available. From the component information, the user can calculate an expected profile for an approximation of the material under analysis, using techniques well known in the art, but described in, for example, "X-ray scattering from semiconductors" by P. F. Fewster, published 2000 by Imperial College Press.

The second step 12 is to obtain an actual x-ray scattering profile of the material, by analysing the sample in, for example, an x-ray reflectometer to produce an x-ray scattering profile for the material.

The third step 14 is to compare the two x-ray scattering profiles over a selected range. That range may be the first 10% of each profile or it can be any desired range as set by the user. When comparing the ranges, error data is generated based upon the differences between the profiles over the selected ranges. At the fourth step 16 the expected x-ray scattering profile is modified according to the error data generated at step 14, in a manner that is well known in the art, but described in, for example, "Fitting of Rocking Curves from Ion-Implanted Semiconductors" by J. G. E. Klappe and P. F. Fewster, published 1994 in J. Appi. Cryst.

At step 18 a check is made to see if the range of the expected x-ray scattering profile substantially matches the range of the actual x-ray scattering profile. How close the match has to be can be set by the user, it is effectively equivalent to saying that the generated error data is below a predetermined threshold. If the two profiles do not match over the range then the user returns to step 14 and steps 14 and 16 are repeated until the ranges of the two profiles substantially match. When this match has occurred the next method step is step 20 where the range is expanded according to a predetermined rubric. Possibilities for this rubric include expansion to a range that is the entire scattering profile, or a stepwise approach to the entire profile. For example, if the range is 1/n of the entire scattering profile (where n is any natural number) then the expanding increases the range by 1/n each time, until in the final pass the range is the entire profile.

At step 22 a second check is made to see if the expected x-ray scattering profile substantially matches the actual x-ray scattering profile. If it does not then the user returns to step 14 and steps 14, 16, 18, 20 and 22 are repeated until the two profiles substantially match. At this point the method terminates at end 24, and the parameters of the material are thereby determined from the parameters used for the last modified expected x-ray scattering profile.

The method of FIG. 1 is carried out in software on a computer with a suitable user interface for the user to input the user defined aspects such as the original approximation and the profile range and range expansion steps. The user, via a display, can watch the progress of the match and receive in due course the result.

Figure 2:
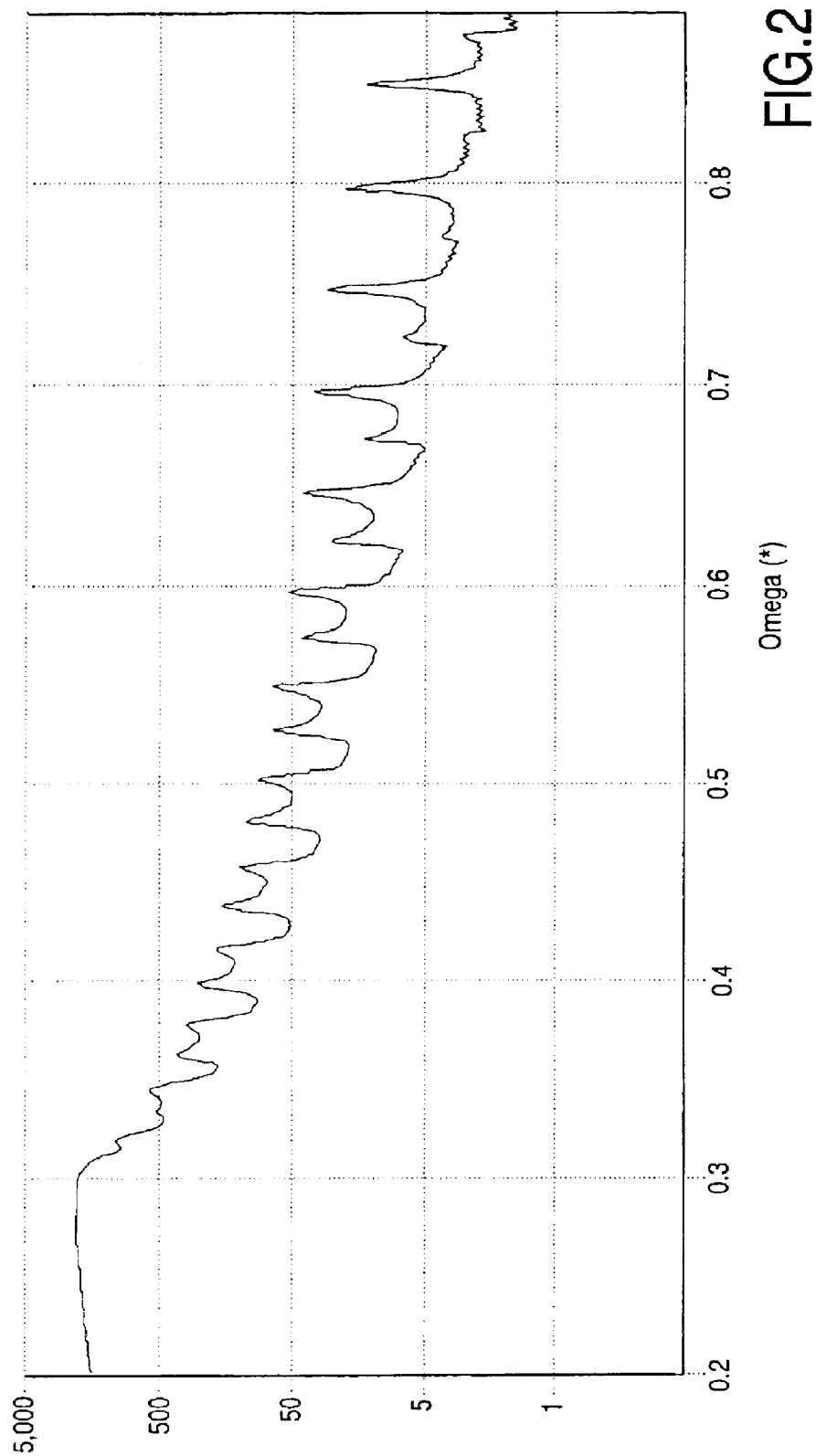
FIG. 2 is an expected x-ray scattering profile for a material.
Figure 3:
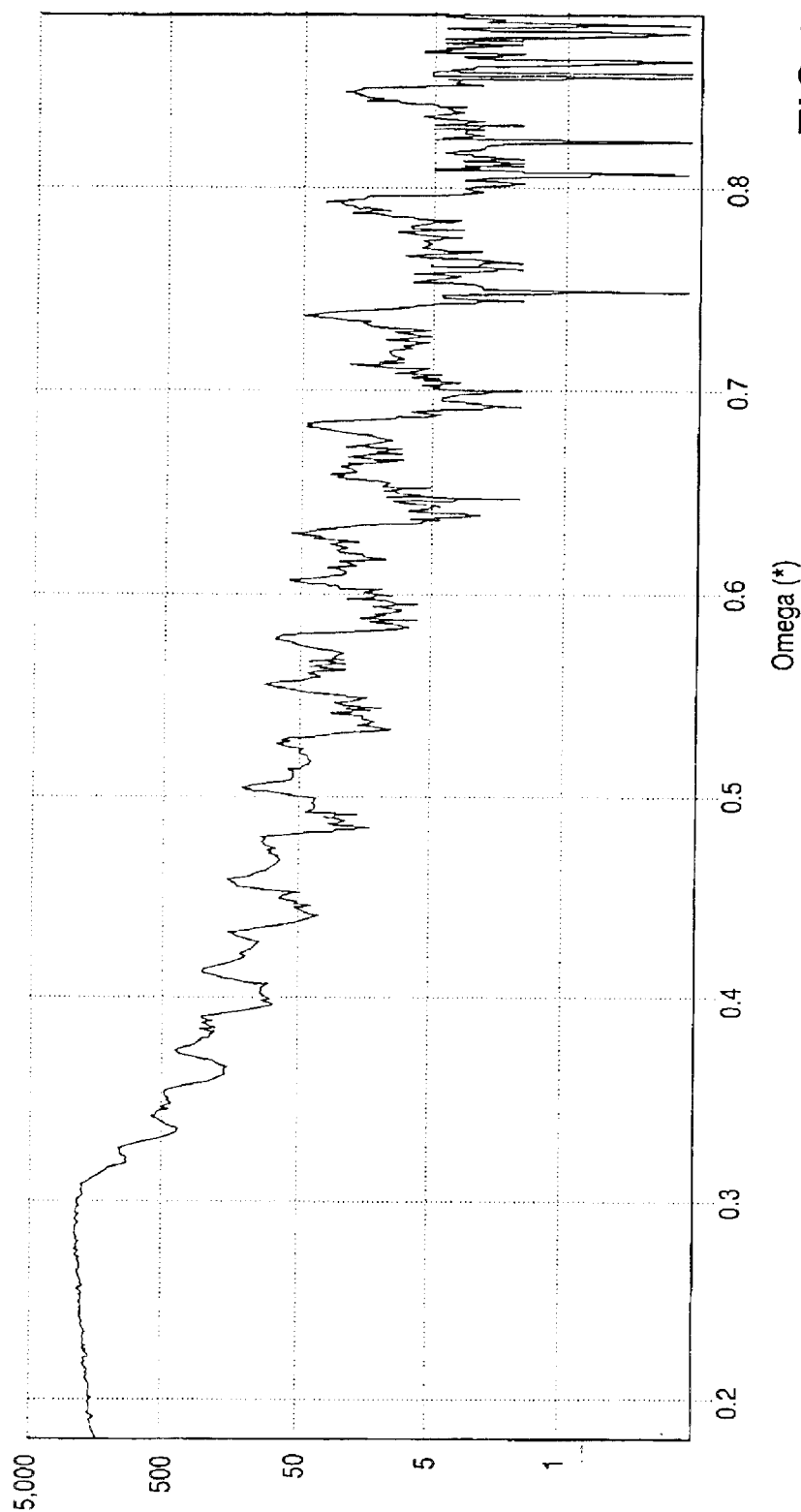
FIG. 3 is an actual x-ray scattering profile for the material of FIG. 2.

FIGS. 2 and 3 show x-ray reflectometry profiles for a particular material sample. Reflectometry is a form of x-ray scattering that involves irradiating the sample with an x-ray at very low angles of incidence. The angle is shown as Omega on the x-axis, with the measured intensity of the reflected beam being shown logarithmically on the y-axis, a conventional arrangement for x-ray reflectometry profiles. The material under analysis is assumed to be composed as follows:

Substrate: GaAs (gallium arsnide)

Superlattice of 8 repeats of the following two layers:
  Layer 1: AlAs (aluminium arsnide) 85 manometers thick
  Layer 2: GaAs 75 manometers thick.

FIG. 2 shows the expected x-ray scattering profile that such a material would generate, and FIG. 3 shows the actual x-ray scattering profile of the material, obtained by analysing the material in a Philips X'Pert MRD machine. As can be seen from the profile of FIG. 3, the actual material differs in its composition from the approximation selected by the user.

The range of the two profiles that is to be compared and matched first is that part of the profiles up to 0.325 deg. This is the less sensitive region of the profiles and also includes that part of the profiles where the scattered intensity is falling rapidly from the critical edge (in this profile around 0.3 deg). Close to this edge, since it has the greatest intensity, the profile describes the general overall structure of the sample. That is, all of the parameters will have to be approximate to the actual values to fit this data in this range. However data existing at higher angles represent the finer detail in the structure and are very sensitive to small parameter changes. This can lead to serious problems associated with false minima. This high angle data can dominate the fitting process and make the possibility of determining the actual parameters very difficult. The procedure is to fit the intensity close to the critical edge by iteratively changing the expected profile and ignoring the high angle data initially. When the profile has been changed to produce the best fit to this range, the range is extended and the model is further refined to produce improved parameters. The range is increased by steps of 0.1 deg each time until the whole of the expected x-ray scattering profile matches the actual scattering profile.

To assist the process of matching the two profiles a number of refinements are used. The first refinement is that prior to the comparing of the profiles a degree of smoothing is applied to the two profiles and then the smoothed profiles are used in the matching process. This degree of smoothing must be reduced to nothing (returning the actual profile to its original form) at some point in the process, either by a series of steps or all at once. This removal of the smoothing ideally takes place after some or most of the matching has occurred. The second is that prior to the comparing of the profiles (and before any smoothing is applied) a genetic algorithm is used to modify the expected x-ray scattering profile. By using the genetic algorithm, the expected profile is brought closer to the actual profile before the main matching process begins. In this way, the original guess by the user is improved prior to the precise fitting of the profiles. Both of these refinements result in an improved process.

What is claimed is:

1. A method for determining parameters of a material, comprising
   a) calculating an expected x-ray scattering profile for an approximation of said material,
   b) obtaining an actual x-ray scattering profile of said material,
   c) comparing a selected range of said expected x-ray scattering profile with a selected range of said actual x-ray scattering profile and generating error data based upon differences between the profiles over the selected ranges,
   d) modifying said expected x-ray scattering profile according to said error data,
   e) repeating steps c) and d) until said selected range of the expected x-ray scattering profile substantially matches said range of the actual x-ray scattering profile,
   f) expanding said selected range of said expected x-ray scattering profile,
   g) repeating steps c) to f) until said expected x-ray scattering profile substantially matches said actual x-ray scattering profile, and thereby determining parameters of the material from the parameters used for the last modified expected x-ray scattering profile.

2. A method according to claim 1, wherein said method step f) comprises expanding the selected range of the expected x-ray scattering profile so that said selected range of the expected x-ray scattering profile is the entire actual x-ray scattering profile.

3. A method according to claim 1, wherein said selected range of the expected x-ray scattering profile is 1/n of the entire actual x-ray scattering profile, where n is any natural number and said expanding increases the range by 1/n each time.

4. A method according to claim 1, wherein, prior to the method step c), a degree of smoothing is applied to the profiles.

5. A method according to claim 1, wherein the modifying of method step d) is achieved by use of an iterative algorithm.

6. A method according to claim 5, wherein said algorithm is a genetic algorithm.

7. A method according to claim 1, wherein said selected range of the expected x-ray scattering profile is a less sensitive region of the actual x-ray scattering profile.

8. A method according to claim 1, wherein the x-ray scattering profiles are x-ray reflectometry profiles.

9. A method according to claim 8, wherein said selected range of the expected x-ray scattering profile includes a portion of the actual x-ray scattering profile where scattered intensity is falling rapidly from a critical edge.

* * * * *